United States Patent [19]

Ghajar

[11] Patent Number: 4,613,324

[45] Date of Patent: Sep. 23, 1986

[54] METHOD AND APPARATUS FOR GUIDING CATHETER INTO VENTRICULAR SYSTEM OF HUMAN BRAIN

[76] Inventor: Jamshid B. G. Ghajar, 435 E. 70th St., New York, N.Y. 10021

[21] Appl. No.: 745,673

[22] Filed: Jun. 17, 1985

[51] Int. Cl.$^4$ ............................................. A61M 31/00
[52] U.S. Cl. .................................. 604/49; 128/303 B; 604/264
[58] Field of Search ............ 604/95, 51, 264, 158–163, 604/174, 175, 302, 49; 128/303 B, 305.3, 329

[56] References Cited

U.S. PATENT DOCUMENTS

| | | | |
|---|---|---|---|
| 3,017,887 | 1/1962 | Heyer | 128/303 B |
| 3,073,310 | 1/1963 | Mocarski | 128/303 B |
| 3,223,087 | 12/1965 | Vladyka et al. | 128/303 B |
| 3,934,590 | 1/1976 | Campagna et al. | 604/302 |

FOREIGN PATENT DOCUMENTS

| | | | |
|---|---|---|---|
| 0722852 | 3/1932 | France | 604/302 |
| 441933 | 12/1974 | U.S.S.R. | 128/303 B |

OTHER PUBLICATIONS

Cooper, The Neurosurgical Alleviation of Parkensonism in *Chemopallidectomy*, 1956, p. 83.

*The Lancet,* Feb. 27, 1960, "New Inventions" by Kendall, p. 474.

*Primary Examiner*—C. Fred Rosenbaum
*Assistant Examiner*—Jerome R. Smith, Jr.
*Attorney, Agent, or Firm*—Henry R. Lerner

[57] ABSTRACT

A method and apparatus are disclosed for accurate insertion of a ventricular catheter through the cranial surface into the ventricular system of the human brain. The method includes providing an orifice through the human cranial surface, cutting and coagulating the dural membranes separating the cerebral substances from the interior cranial surface, and inserting a flexible catheter rendered rigid by incorporation of an obdurator in its lumen, or central cavity, through the cranial orifice and the cerebral substances into a ventricle of the brain. The catheter defines its path of entry into the ventricular system through a guide assembly mounted on the exterior of the cranial surface. The guide assembly is disposed to enable the catheter and incorporated obdurator to enter the cranial orifice and cerebral substances and hence the ventricular system at an angle of 90° in relation to an imaginary plane formed by a tangent to the cranial suface at the point of entry through the orifice. The obdurator is removed from the catheter when the catheter and incorporated obdurator have penetrated the ventricular system.

13 Claims, 6 Drawing Figures

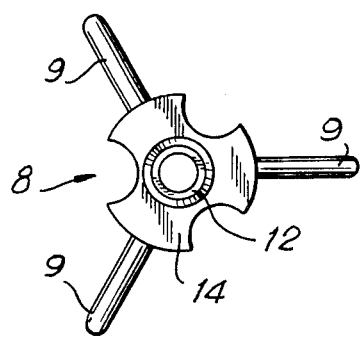
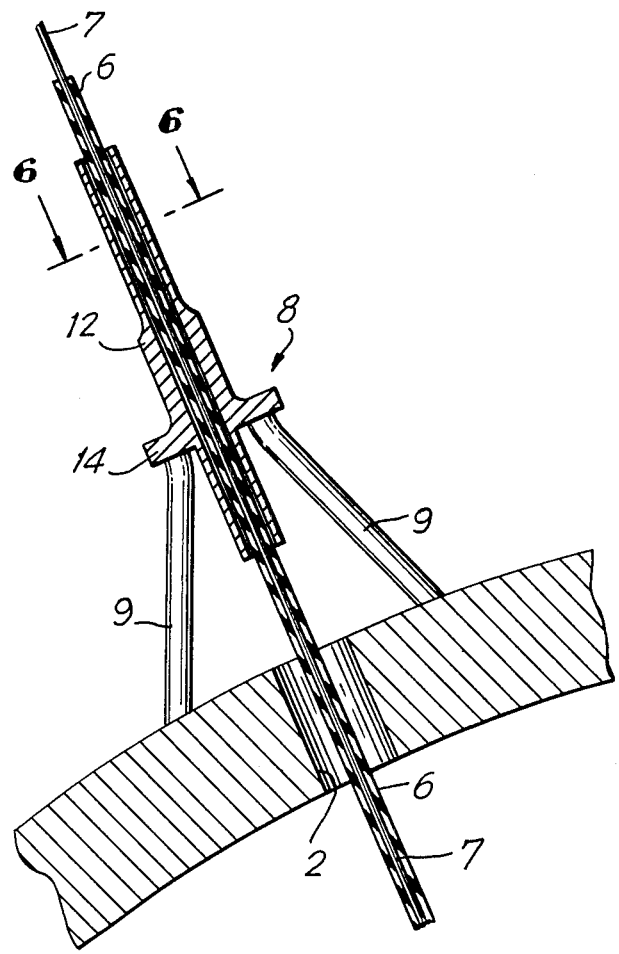
FIG. 4
FIG. 5
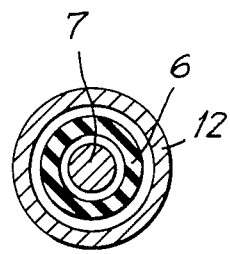
FIG. 6

METHOD AND APPARATUS FOR GUIDING CATHETER INTO VENTRICULAR SYSTEM OF HUMAN BRAIN

BACKGROUND OF THE INVENTION

The four ventricles of the human brain are interconnected cavities that produce and circulate cerebral-spinal fluid (CSF). Procedures involving ventriculostomy, i.e., placement of a catheter into the ventricular system of the brain, form a major part of a neurosurgeon's clinical practice. General areas of application of ventricular catheter placement include intracranial pressure monitoring (ICP), draining or shunting of CSF and the instillation of pharmacological therapeutic agents.

Intracranial pressure monitoring, a monitoring of ventricular pressure, is critical to the management of patients after severe head trauma, fulminant meningitis, Reyes' syndrome, encephalitis, stroke, cerebral hemorrhage, or subarachnoid hemorrhage producing stupor or coma. However, the ventricles are usually compressed after head trauma and thus tehcnically difficult to cannulate for ICP monitoring. Accordingly, subarachnoid pressure monitoring, which is not as true a measure of cerebral pressure as intraventricular pressure monitoring, is generally used.

CSF drainage is essential for patients with congenital or acquired hydrocephalus. CSF drainage, which can only be performed with an intraventricular catheter, is a life-preserving procedure, because it can immediately reduce intracranial pressure. The ventricular catheter, used to drain cerebral-spinal fluid, is connected to a peripheral subcutaneous drainage system, i.e., to the peritoneal cavity or systemic circulation via the heart. In hydrocephalus, the ventricles are enlarged and are an easier target for cannulation. However, recent reports in neurosurgical literature indicate that suboptimal placement in dilated ventricles can subsequently produce catheter obstruction when the ventricles are decompressed and become smaller, thus emphasizing the need for accurate placement.

Catheter placement in cerebral ventricles is widely performed on patients with carcinomatous and fungal meningitis for the administration of well-known antineoplastic and antifungal chemotherapeutic agents, respectively. Invariably, the ventricles in these patients are small or normal sized and difficult to cannulate.

Standard procedures for ventricular catherization are disclosed in the textbook literature. See, for example, *Neurosurgery*, edited by Robert H. Wilkins and Setti S. Rengachary, Section A, Chapter 13, Techniques of Ventricular Puncture (McGraw Hill 1984).

The most frequently chosen site for ventricular catheterization is coronal. In most cases, a catheter is inserted in the anterior horn of the lateral ventricle through an orifice or burr hole drilled just anterior to the coronal suture in the midpupillary line of the cranium, i.e., in the frontal bone over the ventricle. This is known in the field as Kocher's point. The burr hole, only slightly larger than the diameter of the selected catheter to insure a snug fit and provide a seal against CSF leakage, is placed approximately 1 cm. anterior to the coronal suture, approximately 10 to 12 cm. above the nasion, and approximately 2 to 3 cm. from the midline over the nondominant hemisphere. After the burr hole is made, the dura and underlying pia-arachnoid are opened and coagulated, for example, with a fine-tipped blade after cauterizing the dural surface.

A pre-measured catheter having a stylet is then introduced and directed freehand through the burr hole, approximately in the coronal plane, and angled towards the medial canthus of the ipsilateral eye, using external landmarks such as the inner canthus of the eye in the frontal plane and a point just in front of the external auditory meatus in the lateral plane as guides to placement. CSF should flow freely from the catheter tip at a depth of approximately 4 to 5 cm. from the interior cranial surface.

A distinctive "give", or release of opposition, can often be felt when the ventricle is penetrated. Pressure should be measured at this point, since an artifically low value will be obtained even if small amounts of fluid are lost. Then, after removal of the stylet from the catheter, advancement another 1 cm. or so should insure placement in the frontal horn at a depth of about 5 to 6 cm. from the external table of the skull, care being taken that CSF continues to flow.

Intraoperative fluoroscopy and air ventriculography, well known techniques in the art, have been used to confirm freehand catheter placement. While these procedures can be helpful in placing the catheter if the ventricles are small, they also add to the complexity of the overall procedure.

Aside from the cost and time constraints of such radiographic confirmation of catheter placement, many published reports of postoperative studies have revealed misplacement of catheter tips in cerebral matter or subarachnoid space. This misplacement results in increased neurological morbidity and the need for additional operation time. Moreover, multiple passes of the catheter into cerebral matter are quite common before the ventricles are properly penetrated. Finally, the anxiety a neurosurgeon experiences when trying to place a catheter by freehand into the ventricular system makes first pass success that much more difficult and further increases the risks involved in the procedure.

These difficulties have led to a search for a rapid, simple, inexpensive and accurate method and apparatus for cannulating the frontal horn of the lateral ventricle.

SUMMARY OF THE INVENTION

An object of the present invention is to provide a method and apparatus for inserting a catheter through the cranial surface into the anterior horn of the lateral ventricle of the human brain which eliminates the problems, inaccuracies and risks associated with prior art freehand catheter placement.

Another object of the invention is to provide a method and apparatus for inserting a catheter through the cranial surface into the anterior horn of the lateral ventricle of the human brain which optimizes accurate and reproducible placement of the catheter.

Another object of the present invention is to provide a method and apparatus for accurately and reproducibly inserting a catheter through the cranial surface into the anterior horn of the lateral ventricle of the human brain which prevents insertion of the catheter into cerebral matter or subarachnoid space.

These and other objects are attained by a method and apparatus for guiding a catheter from the surface of the human cranium into the anterior horn of the lateral ventricle of the human brain.

The anatomical basis for the present invention lies in the fact that the lateral ventricles of the human brain form an arc parallel to the arc of the cranium, i.e., the contour of the lateral ventricles parallels the arc of the surface of the skull. Thus, a catheter guided perpendicular to the cranium surface at the point of entry into the cranium will enter the ventricular system. Specifically, any line penetrating a burr hole in the surface of the skull at a 90° angle also bisects the lateral ventricle.

The apparatus of the present invention comprises a guide assembly which, when positioned over an orifice drilled in the cranium above the anterior horn of the lateral ventricle, guides a catheter and obdurator through the orifice and into the lateral ventricle at an angle normal to an imaginary plane formed by a tangent to the cranium at the orifice.

The method of the present invention comprises providing an orifice in the cranium just anterior to a coronal suture in a midpupillary line of the cranium and inserting a ventricular catheter containing an obdurator through the orifice towards a lateral ventricle, wherein the catheter containing the obdurator is guided through the orifice, by means of a novel guide assembly, at an angle normal to an imaginary plane formed by a tangent to the cranium at the orifice.

BRIEF DESCRIPTION OF THE DRAWINGS

The method and apparatus of the present invention will now be described with reference to the accompanying drawings, in which:

FIG. 4 is a top plan view of the guide assembly shown in FIG. 3;

FIG. 5 is a section taken along line 5—5 of FIG. 1, on an enlarged scale; and

FIG. 6 is a section taken along line 6—6 of FIG. 5, on an enlarged scale.

DESCRIPTION OF THE PREFERRED EMBODIMENTS

Figure 1:
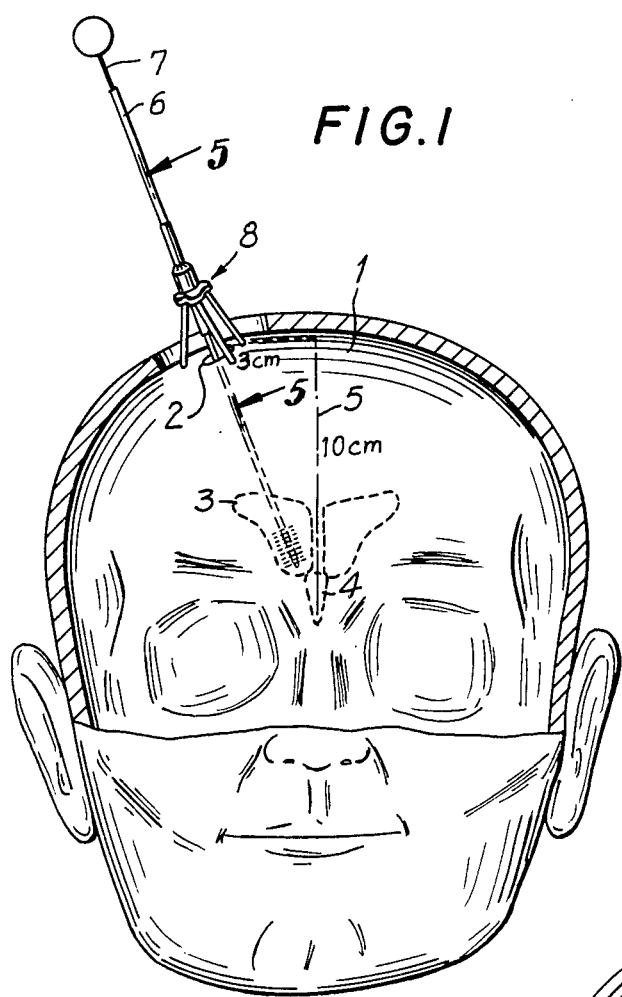
FIG. 1 is a front view of a human skull with a catheter inserted in an anterior horn of a lateral ventricle in accordance with the invention.
Figure 2:
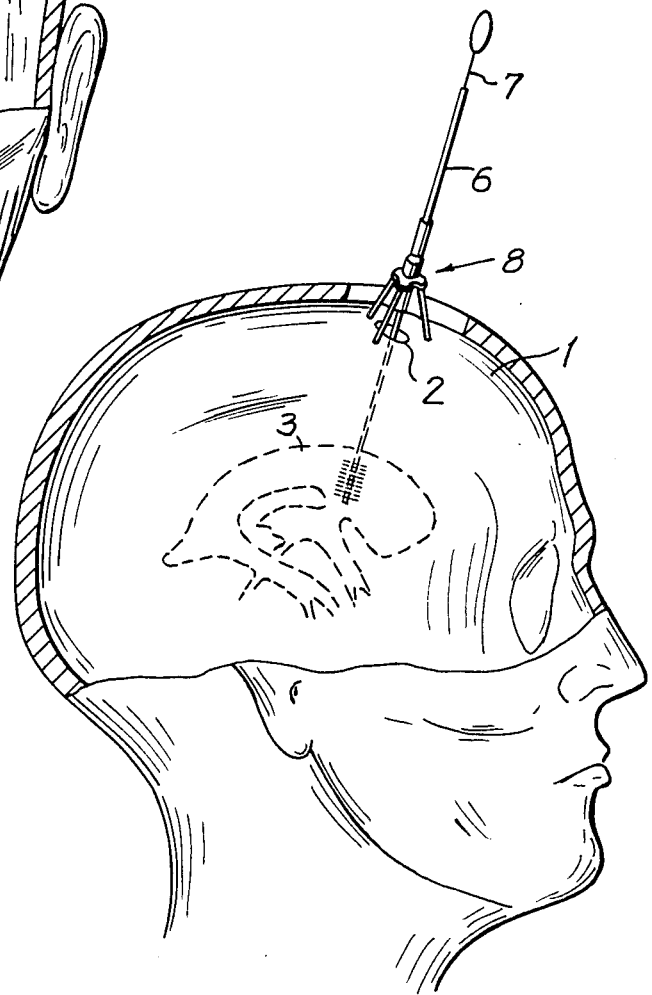
FIG. 2 is a side view of the invention shown in FIG. 1.

FIG. 1 is a front view and FIG. 2 is a side view of the apparatus of the present invention for accurately and reproducibly locating a catheter containing an obdurator in an anterior horn of a lateral ventricle of the human brain.

As shown in FIGS. 1 and 2, an orifice 2, or burr hole, is drilled on the right or left side of a patient's skull 1 in the midpupillary line by conventional techniques. The orifice 2 is located above the anterior horn of lateral ventricle 3, approximately 10 cm. posterior to the nasion 4 and approximately 3 cm. lateral to midline 5 of the skull 1. After drilling of the orifice 2 is complete, the dura and underlying pia-arachnoid (not shown) are cut and coagulated, as is well known in the art.

A catheter 6 containing a rigid obdurator 7 is then accurately guided through the orifice 2 and dural opening into ventricle 3 by guide assembly 8, which is placed and rests on the skull 1 over the orifice 2. Any well known catheter and obdurator, such as the commercially-available Codman Accu-flo ventricular catheter and obdurator, made by Codman and Shurtleff, Inc., may be used in the present invention.

The guide assembly 8 is rigid and non-deformable. The purpose and function of guide assembly 8 necessitates that it be made of a rigid, non-deformable material, such as a rigid plastic or stainless steel.

Figure 3:
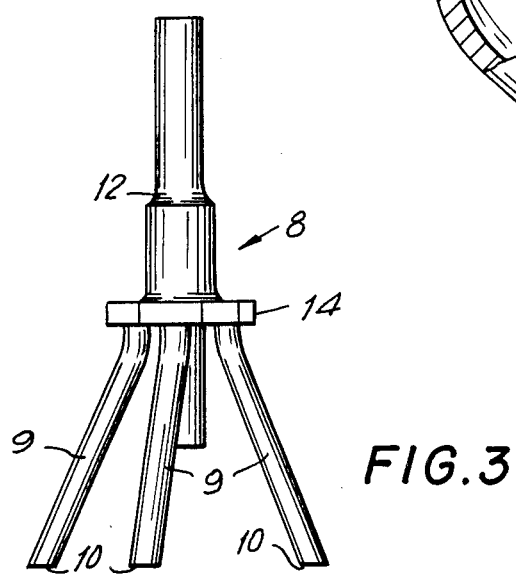
FIG. 3 is a front elevational view of the guide assembly of the present invention.

As shown in FIGS. 3, 4 and 5, guide assembly 8 includes a platform 14. Extending from platform 14 in diverging manner are three legs 9, which terminate in free ends 10. Free ends 10 of legs 9 define a triangle lying in a defined plane. Guide assembly 8 further includes guide means for guiding the catheter 6 in a direction perpendicular to the plane defined by the triangle and through the geometric center of the triangle. As shown in FIGS. 3 and 4, the guide means comprises a tubular member 12 which extends through platform 14 in a direction perpendicular to the plane of the triangle defined by the free ends 10 of legs 9 at the geometric center of this triangle.

Tubular member 12 is hollow, defining a central lumen to allow passage therethrough of the catheter 6 and obdurator 7. The diameter of the central lumen is not critical, but must be sufficient to allow passage of the catheter therethrough. When the guide assembly 8 is placed on the cranial surface with the free ends 10 of legs 9 resting on the cranium and surrounding the burr hole, the plane of the triangle defined by free ends 10 coincides with the imaginary plane tangent to the cranial surface at the burr hole. Accordingly, guide means 12 will direct catheter 6 perpendicularly to said imaginary tangent plane at the center of the burr hole, insuring entry thereof into the ventricular system of the human brain. Subsequent to such entry, the obdurator 7 may be withdrawn, leaving catheter 6 in place to perform its intended function.

Preferably legs 9 of guide assembly 8 are of equal length, equidistantly spaced and symmetrically disposed relative to each other, whereby the free ends 10 define an equilateral triangle, as shown in FIGS. 1 through 4, and the guide means 12 will direct catheter 6 perpendicularly to the plane defined by the equilateral triangle at the geometric center thereof and hence perpendicularly to the imaginary tangent plane at the center of the burr hole. Nevertheless, it is possible to practice the invention with an asymmetrical arrangement of legs, as long as the guide means, tubular member 12 of guide assembly 8, extends perpendicular to the plane defined by the free ends 10 of the legs, and the guide assembly 8 is placed on the cranial surface such that this plane coincides with the imaginary plane tangent to the cranial surface of the burr hole.

Similarly, the invention can be practiced with a guide assembly having more than three legs, as long as the above-described directional criteria are maintained.

While the preferred embodiment of the guide assembly 8 includes a platform 14 for connecting legs 9 to tubular member 12, the platform is not an essential element of guide assembly 8. Thus, legs 9 may be connected directly to tube 12, as long as tubular member 12 guides the catheter 6 in a direction perpendicular to the plane of the triangle formed by the free ends 10 of legs 9 and through the geometric center of said triangle.

Additionally, while tubular member 12 is illustrated as cylindrical, any shape which allows smooth passage of catheter 6 and obdurator 7 therethrough can be employed.

A guide assembly 8 as shown in FIGS. 3 and 4 was made of stainless steel. The guide assembly measured 4.5 cm. in height. The distance between free ends 10 of legs 9 measured 2.5 cm. The central lumen of tubular member 12 had an internal diameter of 2.6 mm.

These dimensions are not critical and can be varied, as long as tubular member 12 is normal to the plane of the triangle defined by free ends 10 of legs 9.

For example, a 2.6 mm. central lumen internal diameter accommodates the commercially available Codman Accu-flo ventricular catheter and obdurator previously mentioned, which has an outer diameter of 2.5 cm. Obviously, the invention is not limited in this regard and catheters of different diameters can be used, with corresponding changes in the diameter of the central lumen of tubular member 12. Since most catheters range from about 2 mm. to about 4 mm. in outer diameter, a preferred range of internal diameter for the central lumen of tubular member 12 is about 1 mm. to about 5 mm. It is also within the scope of the invention to provide one or more inserts, telescopically receivable within tubular member 12, to accommodate smaller diameter catheters.

Similarly, the height of guide assembly 8 and the distance between free ends 10 of legs 9 can be varied, as long as the following principles are observed. First, the base of the guide assembly must preferably form an equilateral triangle defined by the free ends 10 of legs 9. Second, a line through the central lumen of tubular member 12 must be normal to the plane of the triangle defined by the free ends 10 of legs 9 and must pass through the geometric center thereof.

Preferably, the distance between free ends 10 of legs 9 ranges from about 1 cm. to about 6 cm. The lower limit is established based on the smallest burr hole or orifice necessary for passing a catheter therethrough. The upper limit is established based on the change in skull curvature which occurs when one crosses the midline 5 of the skull 1. Specifically, since the orifice or burr hole 2 is drilled generally from about 2 cm. to about 3 cm. from the midline 5, the upper limit of about 6 cm. is preferred so that a leg 9 does not rest on skull 1 at a point beyond the midline 5 where the skull curvature has changed. This would place the guide assembly 8 at such an angle that tubular member 12 would not be directed normal to the imaginary plane defined by a tangent to the orifice 2 at the point of entry.

While a specific height for the guide assembly has been exemplified, this is not a critical parameter. A preferred height range for guide assembly 8 is about 2 cm. to about 10 cm. The lower limit is established based on a minimum central lumen length necessary for guidance accuracy. The upper limit is established on the basis of the usual length of a catheter (15 cm.) minus the standard intracranial distance to the ventricle (5 cm.).

Similarly, although the guide assembly 8 of the present invention has been illustrated with three legs 9, this is not a critical limitation. For example, the guide assembly 8 of the present invention may be made with four legs. In such an embodiment, the free ends of the four legs define the corners of a square or rectangle, the axis of tubular member 12 passes through the geometric center of the square or rectangle, and said axis is normal to the plane of the square or rectangle.

The efficacy of the present invention was evaluated in seventeen patients who required ventriculostomy. Nine of the patients had normal or smaller ventricles (less than 3 mm. width of the anterior horn). The age range was 12 to 78. Nine patients were diagnosed for carcinomatous meningitis and seven for hydrocephalus. One patient had a caudate tumor lateral to the anterior horn and cannulation of the ventricle was used as a fluoroscopic reference point for tumor biopsy.

Using the method and apparatus of the present invention, cerebral-spinal fluid was obtained in all patients on the first pass of the catheter at an approximate intracranial distance of about 5 cm. Confirmation of catheter placement in the ipsilateral anterior horn of the lateral ventricle was made by intraoperative fluoroscopy or postoperative CT scan.

The method and apparatus of the present invention insures optimal ventricular catheter placement. It can be used in any situation requiring placement of a catheter in the ventricular system, e.g., intracranial pressure monitoring, drainage or shunting of cerebral-spinal fluid and the installation of pharmacologic therapeutic agents. Moreover, the present invention is so anatomically consistent that it can be employed as a reference point for biopsy of brain lesions.

The present invention eliminates the anxiety ordinarily experienced by neurosurgeons when passing a catheter. Patient care is improved by eliminating complications and associated morbidity. A reduction in cost of the patient is achieved by eliminating the need for intraoperative radiographic monitoring and by decreasing operating room time.

It will be understood that the specification and preferred embodiments are illustrative but not limitative of the present invention. Other embodiments within the spirit and scope of the invention will suggest themselves to those skilled in the art.

Having thus described by invention, what I claim and desire to secure by letters patent is:

1. An apparatus for accurately and reproducibly inserting a catheter through an orifice drilled in a human cranium and guiding said catheter into a ventricle of a human brain, said apparatus comprising,
   (a) tubular means adapted to receive and guide said catheter therethrough,
   (b) support means for said tubular means, said support means being adapted to rest unsecured on said human cranium in surrounding spaced relation to said orifice,
   (c) said support means and said tubular means being related to each other and to said cranium so as to guide said catheter through said orifice and in a direction perpendicular to an imaginary plane defined by a tangent to the cranium of said orifice, independent of the orientation of the orifice,
   (d) said tubular means adapted to be in guiding engagement with said catheter while the free end of said catheter is inserted into said human brain.

2. An apparatus according to claim 1, wherein said support means comprises a plurality of legs.

3. An apparatus according to claim 2, wherein said plurality of legs comprises three legs terminating in free ends, said free ends forming a triangle defining a plane, said tubular means guiding said catheter through said orifice in a direction perpendicular to the plane defined by said triangle and through the geometric center of said triangle.

4. An apparatus according to claim 3, wherein said legs are of equal length and said triangle is an equilateral triangle.

5. An apparatus according to claim 1, wherein said support means is connected to said tubular means through a connecting platform.

6. An apparatus according to claim 1, wherein said apparatus is made of a rigid plastic or stainless steel.

7. An apparatus according to claim 4, wherein said apparatus has a height ranging from about 2 cm. to about 10 cm., the distance between said free ends of said legs ranges from about 1 cm. to about 6 cm., and said tubular member has an inner diameter ranging from about 1 mm. to about 5 mm.

8. An apparatus according to claim 1, including removable insert means adapted to be placed within said tubular means for decreasing the inner diameter of said tubular means.

9. A method of inserting a ventricular catheter into a ventricle within a human cranium comprising:
 (a) drilling an orifice in the cranium just anterior to a coronal suture in a midpupillary line of the cranium,
 (b) guiding the catheter through the orifice by means of a guide assembly in a direction perpendicular to an imaginary plane defined by a tangent to the cranium at the orifice, whereby the catheter accurately penetrates the ventricle on the first insertion,
 (c) said guide assembly comprising tubular means and support means for said tubular means, said method further comprising placing said support means so as to rest unsecured on said human cranium in surrounding spaced relation to said orifice, and guiding said catheter through said tubular means and into said orifice and said ventricle, said support means and said tubular means being related to each other such that said catheter is guided through said orifice by said tubular means in a direction perpendicular to an imaginary plane defined by a tangent to the cranium of the orifice, independent of said orifice.

10. A method according to claim 9 further comprising supporting said tubular means through a support means comprising a plurality of legs.

11. A method according to claim 10 wherein said tubular means is supported through a support means comprising three legs terminating in free ends, said free ends forming a triangle defining a plane, said method comprising guiding said catheter through said tubular means and into said orifice and ventricle in a direction perpendicular to the plane defined by said triangle and through the geometric center of said triangle.

12. A method according to claim 11, wherein said legs are of equal length and said triangle is an equilateral triangle.

13. A method according to claim 9 including inserting a removable insert within said tubular means to reduce the diameter thereof.

* * * * *

UNITED STATES PATENT AND TRADEMARK OFFICE
CERTIFICATE OF CORRECTION

PATENT NO. : 4,613,324
DATED : September 23, 1986
INVENTOR(S) : Jamshid B. G. Ghajar It is certified that error appears in the above-identified patent and that said Letters Patent is hereby corrected as shown below:

In Claim 1, column 6, line 45:

"of" should read --at--

In Claim 9, column 8, line 5:

"of" first occurrence, should read --at--

Signed and Sealed this

Twentieth Day of January, 1987

Attest:

DONALD J. QUIGG

Attesting Officer

Commissioner of Patents and Trademarks